United States Patent
Wu et al.

(10) Patent No.: US 11,654,317 B2
(45) Date of Patent: May 23, 2023

(54) MICROBACTERIUM OLEIVORANS CAPABLE OF DEGRADING POLYETHYLENE TEREPHTHALATE AND INTERMEDIATE THEREOF

(71) Applicant: Jiangnan University, Wuxi (CN)

(72) Inventors: Jing Wu, Wuxi (CN); Zhengfei Yan, Nanjing (CN); Lengtao Gu, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 333 days.

(21) Appl. No.: 16/993,382

(22) Filed: Aug. 14, 2020

(65) Prior Publication Data
US 2020/0384300 A1 Dec. 10, 2020

(30) Foreign Application Priority Data

Nov. 21, 2019 (CN) .......................... 201911147762.3

(51) Int. Cl.
*A62D 3/02* (2007.01)
*C12N 1/20* (2006.01)
*A62D 101/28* (2007.01)
*C12R 1/01* (2006.01)

(52) U.S. Cl.
CPC ............ *A62D 3/02* (2013.01); *A62D 2101/28* (2013.01); *C12N 1/205* (2021.05); *C12R 2001/01* (2021.05)

(58) Field of Classification Search
None
See application file for complete search history.

(56) References Cited

PUBLICATIONS

Barth et al., "Effect of hydrolysis products on the enzymatic degradation of polyethylene terephthalate nanoparticles by a polyester hydrolase from Thermobifida fusca", Biochemical Engineering Journal 93:222-228, 2015 (Year: 2015).*

* cited by examiner

*Primary Examiner* — David Steadman
(74) *Attorney, Agent, or Firm* — Ipro, PLLC

(57) ABSTRACT

The present disclosure discloses *Microbacterium oleivorans* capable of degrading polyethylene terephthalate and an intermediate thereof, and belongs to the technical field of microorganisms. The present disclosure provides *Microbacterium oleivorans* JWG-G2 capable of degrading the polyethylene terephthalate. After *Microbacterium oleivorans* JWG-G2 is inoculated into an inorganic salt liquid medium containing 2 g/L polyethylene terephthalate plastic particles with an inoculation quantity of $1 \times 10^8$ CFU/mL to be cultivated for 5 d, the polyethylene terephthalate plastic particles can be partially degraded into monohydroxyethyl terephthalate and terephthalic acid capable of being directly recycled, ester bond functional groups on surfaces of the polyethylene terephthalate plastic particles can be reduced, and a weight loss ratio of the polyethylene terephthalate plastic particles can reach 5.6%. Therefore, *Microbacterium oleivorans* JWG-G2 of the present disclosure has an extremely high application prospect in degradation of the polyethylene terephthalate.

7 Claims, 4 Drawing Sheets

Specification includes a Sequence Listing.

MICROBACTERIUM OLEIVORANS CAPABLE OF DEGRADING POLYETHYLENE TEREPHTHALATE AND INTERMEDIATE THEREOF

REFERENCE TO SEQUENCE LISTING

The instant application contains a Sequence Listing which was submitted in ASCII format via EFS-Web and is hereby incorporated by reference in its entirety. Said ASCII Copy, created on Jul. 27, 2020, is named "seq.txt" and is 2,257 bytes in size.

TECHNICAL FIELD

The present disclosure relates to *Microbacterium oleivorans* capable of degrading polyethylene terephthalate and an intermediate thereof, and belongs to the technical field of microorganisms.

BACKGROUND

With the rapid development of economy, people's consumption level of plastic products has been significantly increased. The global annual plastic consumption exceeds 320 million tons, and the annual growth rate of this plastic consumption is 4% to 6%. However, because plastics are difficult to degrade, the global annual recycling rate of the plastic products is only 14%, which makes plastic waste continue to accumulate in the environment, causing a serious ecological threat.

Polyethylene terephthalate (PET) is a linear macromolecule formed by sequentially connecting ethylene glycol (EG) and terephthalic acid (TPA) through ester bonds. At present, PET plastic products account for about 60% of all plastic products, and correspondingly, PET plastic waste also accounts for a relatively high proportion in all plastic waste. Therefore, degradation of the PET is very critical to treatment of the plastic waste.

At present, people still stay at the stage of degrading the PET by using traditional chemical degradation methods such as acidolysis, alkaline hydrolysis or alcoholysis or physical degradation methods such as pyrolysis. However, the chemical degradation methods require the use of a large number of chemicals, and the physical degradation methods require high-temperature and high-pressure equipment, which greatly increases the cost of treating the PET. Moreover, a large number of toxic and harmful substances will be produced in the process of degrading the PET by utilizing the chemical degradation methods, and these toxic and harmful substances will have a relatively serious negative impact on an ecological environment, which makes the degradation of the PET be not worth the candle. Therefore, new technologies for degrading the PET are still being energetically explored around the world.

A biodegradation technology is a technology for directly degrading the plastics through strains capable of degrading the plastics, and gradually becomes a research hotspot in the field of plastic degradation due to its green pollution-free and low-cost advantages. For example, an ochrobactrum strain capable of degrading polylactic acid (PLA) is recorded in a patent application text with the publication number CN102639690A. Zhou et al. found a penicillium strain capable of degrading polyhydroxyalkanoate (PHA) (specifically see the reference: Polymer-plastics Technology and Engineering, 2009, 48 (1): 58-63).

However, compared with bio-based plastics such as the C—O bond connected PHA and PLA, PET molecular chains contain a large number of aromatic groups, which results in large steric hindrance and a more hydrophobic surface of the PET molecular chains, being difficult to degrade by the microorganisms. Therefore, obtaining a strain capable of degrading the PET is still a difficulty.

SUMMARY

The present disclosure provides *Microbacterium oleivorans* capable of degrading polyethylene terephthalate and an intermediate thereof.

The present disclosure provides *Microbacterium oleivorans* JWG-G2. *Microbacterium oleivorans* JWG-G2 is preserved in the China Center for Type Culture Collection, with the preservation number of CCTCC NO: M 2019416, and the preservation date of Jun. 3, 2019.

*Microbacterium oleivorans* JWG-G2 is separated from a soil sample from the Taohuashan landfill in Wuxi. Through sequencing analysis, a 16S rDNA sequence of the strain is shown as SEQ ID NO: 1. A sequence obtained by sequencing is subjected to nucleotide sequence comparison in Genbank. A result shows that a similarity to a nucleotide sequence of a *Microbacterium* is up to 99%. Strains with the high similarity to the sequence constitute a phylogenetic tree (specifically see FIG. 1). A result shows that the strain belongs to *Microbacterium oleivorans* of genus *Microbacterium*, and is named *Microbacterium oleivorans* JWG-G2.

Bacterial colonies of *Microbacterium oleivorans* JWG-G2 on an LB solid medium are shaped like rounded raised protrusions, and are light golden yellow, not transparent, smooth in surface, wet and glossy, and regular in edge (specifically see FIG. 2).

The present disclosure further provides applications of the above *Microbacterium oleivorans* JWG-G2 to degradation of polyethylene terephthalate and/or an intermediate of the polyethylene terephthalate.

In one embodiment of the present disclosure, the intermediate of the polyethylene terephthalate is monohydroxyethyl terephthalate and/or bis(2-hydroxyethyl) terephthalate.

The present disclosure further provides a method for degrading polyethylene terephthalate and/or an intermediate of the polyethylene terephthalate. The method is to inoculate the above *Microbacterium oleivorans* JWG-G2 into a medium containing the polyethylene terephthalate and/or the intermediate of the polyethylene terephthalate for cultivation.

In one embodiment of the present disclosure, the medium is a liquid medium.

In one embodiment of the present disclosure, the intermediate of the polyethylene terephthalate is monohydroxyethyl terephthalate and/or bis(2-hydroxyethyl) terephthalate.

In one embodiment of the present disclosure, an inoculation quantity of the above *Microbacterium oleivorans* JWG-G2 in the medium containing the polyethylene terephthalate and/or the intermediate of the polyethylene terephthalate is not less than $1 \times 10^8$ CFU/mL.

In one embodiment of the present disclosure, in the medium containing the polyethylene terephthalate, a content of the polyethylene terephthalate is not greater than 2 g/L.

In one embodiment of the present disclosure, in the medium containing the intermediate of the polyethylene terephthalate, a content of the intermediate of the polyethylene terephthalate is not greater than 0.2 g/L.

In one embodiment of the present disclosure, in the medium containing the polyethylene terephthalate and the intermediate of the polyethylene terephthalate, a total content of the polyethylene terephthalate and the intermediate of the polyethylene terephthalate is not greater than 2.2 g/L.

In one embodiment of the present disclosure, the medium is an inorganic salt medium.

The present disclosure further provides a product capable of being used for degrading polyethylene terephthalate and/or an intermediate of the polyethylene terephthalate. The product contains the above *Microbacterium oleivorans* JWG-G2.

The present disclosure provides *Microbacterium oleivorans* JWG-G2 capable of degrading the polyethylene terephthalate (PET). After *Microbacterium oleivorans* JWG-G2 is inoculated into an inorganic salt liquid medium containing 2 g/L PET plastic particles with an inoculation quantity of $1\times10^8$ CFU/mL to be cultivated for 5 d, the PET plastic particles can be partially degraded into monohydroxyethyl terephthalate (MHET) and terephthalic acid (TPA) capable of being directly recycled, ester bond functional groups on surfaces of the PET plastic particles can be reduced, and a weight loss ratio of the PET plastic particles can reach 5.6%. Therefore, *Microbacterium oleivorans* JWG-G2 of the present disclosure has an extremely high application prospect in degradation of the PET.

The present disclosure provides *Microbacterium oleivorans* JWG-G2 capable of degrading the intermediate of the PET. After *Microbacterium oleivorans* JWG-G2 is inoculated into an inorganic salt liquid medium containing 0.2 g/L MHET with an inoculation quantity of $1\times10^8$ CFU/mL to be cultivated for 5 d, the MHET can be partially degraded into the TPA capable of being directly recycled, and a weight loss ratio of the MHET can reach 4.5%. After *Microbacterium oleivorans* JWG-G2 is inoculated into an inorganic salt liquid medium containing 0.2 g/L bis(2-hydroxyethyl) terephthalate (BHET) with an inoculation quantity of $1\times10^8$ CFU/mL to be cultivated for 5 d, the BHET can be partially degraded into the MHET and the TPA capable of being directly recycled, and a weight loss ratio of the BHET can reach 11.2%. Therefore, *Microbacterium oleivorans* JWG-G2 of the present disclosure has an extremely high application prospect in degradation of the intermediate of the PET.

The present disclosure provides *Microbacterium oleivorans* JWG-G2, which can degrade starch and liquidize gelatin. Moreover, *Microbacterium oleivorans* JWG-G2 has excellent salt resistance and can vigorously grow in LB liquid mediums containing 1 to 9 g/L NaCl.

Biological Material Preservation

*Microbacterium oleivorans* JWG-G2 is taxonomically named *Microbacterium oleivorans*, and has been preserved in the China Center for Type Culture Collection on Jun. 3, 2019, with the preservation number of CCTCC NO: M 2019416 and the preservation address of Wuhan University, Wuhan, China.

DETAILED DESCRIPTION

Figure 1:
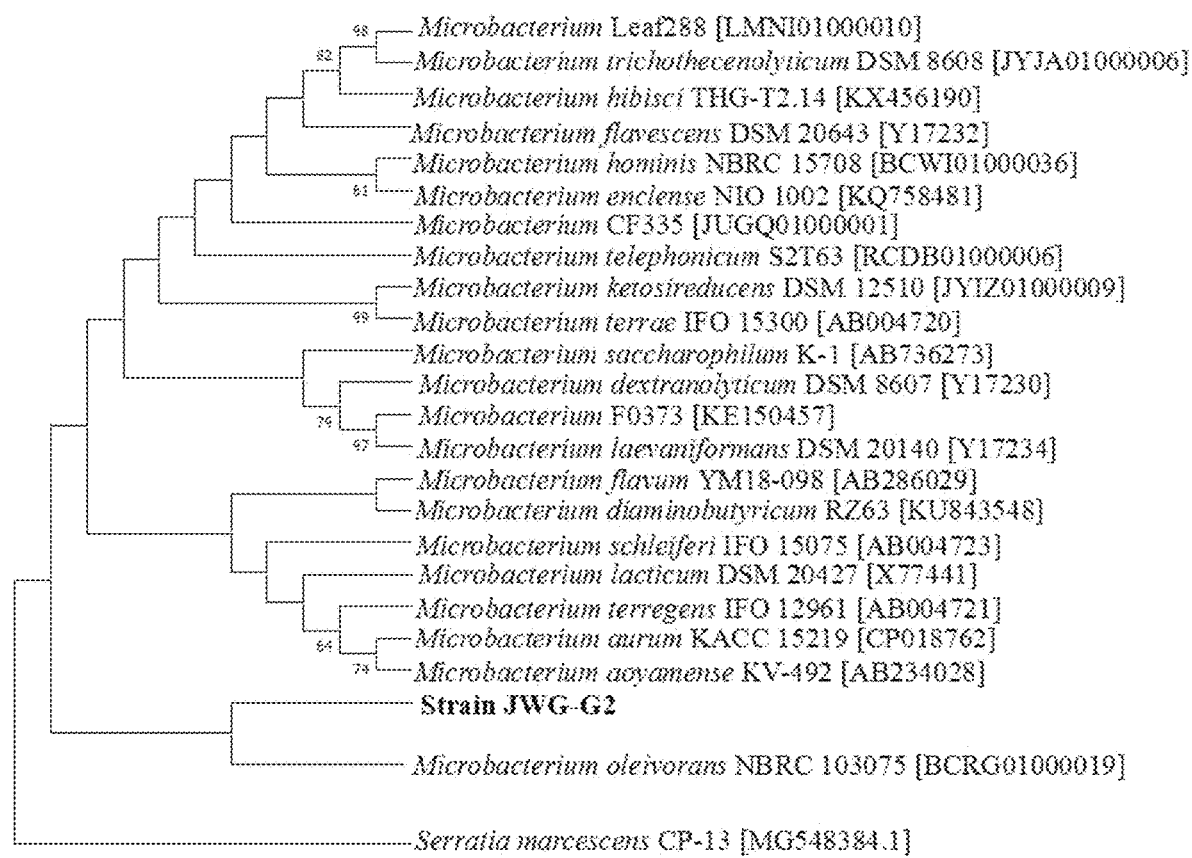
FIG. 1 is a phylogenetic tree of *Microbacterium oleivorans* JWG-G2.

The present disclosure is further expounded below in combination with specific examples.

Dimethyl terephthalate (DET), polyethylene terephthalate (PET) plastic particles, monohydroxyethyl terephthalate (MHET), bis(2-hydroxyethyl) terephthalate (BHET) and terephthalic acid (TPA) involved in the following examples are purchased from Sigma Company.

Mediums Involved in the Following Examples are as Follows:

LB solid medium (g/L): 10 g of peptone, 5 g of yeast powder, 10 g of sodium chloride, 20 g of agar, and pH 7.0.

LB liquid medium (g/L): 10 g of peptone, 5 g of yeast powder, 10 g of sodium chloride, and pH 7.0.

Inorganic salt liquid medium containing DET (g/L): 0.7 g of $KH_2PO_4$, 0.5 g of $K_2HPO_4.3H_2O$, 2 g of $NH_4Cl$, 0.6 g of $MgSO_4.7H_2O$, 0.005 g of NaCl, 0.001 g of $FeSO_4.7H_2O$, 0.002 g of $ZnSO_4.7H_2O$, 0.001 g of $MnSO_4.H_2O$, and 2 g of the DET.

Inorganic salt solid medium containing PET (g/L): 0.7 g of $KH_2PO_4$, 0.5 g of $K_2HPO_4.3H_2O$, 2 g of $NH_4Cl$, 0.6 g of $MgSO_4.7H_2O$, 0.005 g of NaCl, 0.001 g of $FeSO_4.7H_2O$, 0.002 g of $ZnSO_4.7H_2O$, 0.001 g of $MnSO_4.H_2O$, 2 g of PET plastic particles, and 20 g of agar powder.

Inorganic salt liquid medium containing PET (g/L): 0.7 g of $KH_2PO_4$, 0.5 g of $K_2HPO_4.3H_2O$, 2 g of $NH_4Cl$, 0.6 g of $MgSO_4.7H_2O$, 0.005 g of NaCl, 0.001 g of $FeSO_4.7H_2O$, 0.002 g of $ZnSO_4.7H_2O$, 0.001 g of $MnSO_4.H_2O$, and 2 g of the PET.

Inorganic salt liquid medium containing a PET intermediate (g/L): 0.7 g of $KH_2PO_4$, 0.5 g of $K_2HPO_4.3H_2O$, 2 g of $NH_4Cl$, 0.6 g of $MgSO_4.7H_2O$, 0.005 g of NaCl, 0.001 g of $FeSO_4.7H_2O$, 0.002 g of $ZnSO_4.7H_2O$, 0.001 g of $MnSO_4.H_2O$, and 0.2 g of the PET intermediate (BHET or MHET).

Inorganic salt solid medium without a nutrient source (g/L): 0.7 g of $KH_2PO_4$, 0.5 g of $K_2HPO_4.3H_2O$, 2 g of $NH_4Cl$, 0.6 g of $MgSO_4.7H_2O$, 0.005 g of NaCl, 0.001 g of $FeSO_4.7H_2O$, 0.002 g of $ZnSO_4.7H_2O$, 0.001 g of $MnSO_4.H_2O$, and 20 g of agar powder.

Detection Methods Involved in the Following Examples are as Follows:

Detection Method of Changes of Functional Groups on Surfaces of Polyethylene Terephthalate (PET) Plastic Particles:

The PET plastic particles treated by a strain are repeatedly cleaned with deionized water 3 to 4 times. The cleaned PET plastic particles are subjected to ultrasonic for 15 min at a power of 200 W and a frequency of 58 KHz. The PET plastic particles after ultrasonic are placed into a dryer to be dried for 6 h at 60° C. With the PET plastic particles not treated as control, a Fourier transform infrared spectrometer is utilized to detect the changes of the functional groups on the surfaces of the PET plastic particles not treated and the surfaces of the PET plastic particles treated by the strain.

Detection Methods of Degradation Products and Contents Thereof:

Standard treatment: Standards of TPA, MHET and BHET are weighed respectively to be dissolved in dimethylsulfoxide (DMSO) to prepare mother solutions, and the mother solutions are diluted into 0.1 mg/mL standard solutions by sterile water, filtered by a 0.22 μM filtering head, and injected into liquid phase bottles by an injector for HPLC detection.

Sample treatment: A cultivation solution is subjected to still standing for 10 min, and 5 mL of a supernatant is taken, centrifuged for 8 min at 12,000 rpm, filtered by a 0.22 μM filtering head, and injected into a liquid phase bottle by an injector for HPLC detection.

Detection Method of Weight Loss Ratio:

A weight loss ratio (%) of PET plastic particles=
$[(m2-m1) \div m2] \times 100$.

m1: The PET plastic particles treated by a strain are repeatedly cleaned with deionized water 3 to 4 times. The cleaned PET plastic particles are subjected to ultrasonic for 15 min at a power of 200 W and a frequency of 58 KHz, placed into a dryer to be dried for 6 h at 60° C., and then weighed.

m2: The PET plastic particles before being treated by the strain are repeatedly cleaned with deionized water 3 to 4 times. The cleaned PET plastic particles are subjected to ultrasonic for 15 min at a power of 200 W and a frequency of 58 KHz, placed into a dryer to be dried for 6 h at 60° C., and then weighed.

A weight loss ratio (%) of a PET intermediate=
$\{[(c1-c2) \times v2] \div (c1 \times v1)\} \times 100$.

c1: A concentration of a PET intermediate in a reaction system before a reaction, mg/L.

v1: A concentration of the PET intermediate in the reaction system before the reaction, L.

c1: A concentration of a PET intermediate in a reaction system after the reaction, mg/L.

v1: A concentration of the PET intermediate in the reaction system after the reaction, L.

Example 1: Screening and Identification of *Microbacterium oleivorans*

Specific steps are as follows:

1. Screening

With soil from the Taohuashan landfill in Wuxi as a sample, 1 g of landfill soil is taken, added into 9 mL of an inorganic salt liquid medium containing 2 g/L DET, and subjected to shaking enrichment culture for 48 h at 35° C. and 180 rpm. Then, 1 mL of above enrichment liquid is sucked, added into 9 mL of a new inorganic salt liquid medium containing 2 g/L DET and cultivated for 10 cycles at the same conditions. Cultivation solutions obtained after 10 cycles of cultivation are subjected to still standing for 15 min, $10^{-4}$, $10^{-5}$ and $10^{-6}$ diluents obtained by sequentially diluting 1 mL of supernatants and $10^{-4}$, $10^{-5}$ and $10^{-6}$ diluents obtained by diluting 200 μL of supernatants evenly coat inorganic salt solid mediums containing 2 g/L PET, and the mediums are placed in a 35° C. incubator for constant-temperature cultivation until bacterial colonies grow out. With an inorganic salt solid medium without a nutrient source as control, the bacterial colonies are picked to streak inorganic salt solid mediums containing 2 g/L PET and cultivated at 35° C., several times of repeated streaking are conducted to obtain non-autotrophic purified strains, and 4 non-autotrophic purified strains growing best are named a strain JWG-G2, a strain JWG-G5, a strain JWG-HD2 and a strain JWG-YR2 respectively.

2. Identification

Total DNA of the strain JWG-G2, the strain JWG-G5, the strain JWG-HD2 and the strain JWG-YR2 is extracted for 16S rDNA amplification and sequencing (completed by Wuxi TianLin Biotechnology Co., Ltd.). Sequencing results show that the 16S rDNA similarity rate of the above 4 non-autotrophic purified strains is 100%. It can be seen that the above 4 non-autotrophic purified strains are all differentiated from 4 single bacterial colonies of the same strain. Therefore, the strain JWG-G2 is selected as an identification object for next step identification (the 16S rDNA sequence of the JWG-G2 is shown as SEQ ID NO: 1).

Sequences obtained by sequencing are subjected to nucleotide sequence comparison in Genbank. It is found that the 16S rDNA sequence homology of the strain JWG-G2 to a *Microbacterium* is greater than 99%, and the 16S rDNA sequence similarity rate to *Microbacterium oleivorans* NBRC103075 reaches 99.5%. It can be seen that the strain JWG-G2 belongs to genus *Microbacterium*.

The 16S rDNA sequence of the strain JWG-G2 and other high-similarity strains constitute a phylogenetic tree (see FIG. 1 for the phylogenetic tree constituted by the strain JWG-G2). Results show that the strain JWG-G2 and *Microbacterium oleivorans* NBRC103075 belong to the same branch. It can be seen that the strain JWG-G2 belongs to *Microbacterium oleivorans*, and is named *Microbacterium oleivorans* JWG-G2.

Example 2: Cultivation of *Microbacterium oleivorans*

Figure 2:
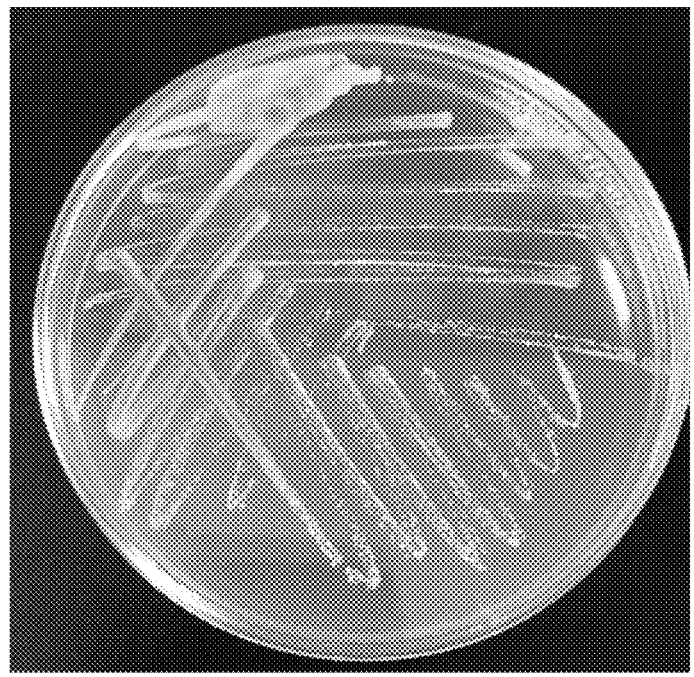
FIG. 2 is bacterial colonies of the *Microbacterium oleivorans* JWG-G2.

Specific steps are as follows:

A ring of *Microbacterium oleivorans* JWG-G2 obtained in Example 1 is scraped and inoculated into an LB solid medium for streaking cultivation. After cultivation for 36 h at 35° C., their bacterial colonies are observed, and it is found that their bacterial colonies are shaped like rounded raised protrusions, and are light red, not transparent, smooth in surface, wet and glossy, and regular in edge (specifically see FIG. 2).

*Microbacterium oleivorans* JWG-G2 obtained in Example 1 is observed under a microscope after Gram staining. It is found that *Microbacterium oleivorans* JWG-G2 is a Gram-positive bacterium.

A ring of *Microbacterium oleivorans* JWG-G2 obtained in Example 1 is scraped and inoculated into LB liquid mediums with pH being 3 to 10 respectively to be cultivated. After cultivation for 36 h at 35° C., $OD_{600}$ values in cultivation solutions are detected through a microplate reader. It is found that suitable growth pH of *Microbacterium oleivorans* JWG-G2 is 6.5 to 8.5, and the most suitable growth pH is 7.

A ring of *Microbacterium oleivorans* JWG-G2 obtained in Example 1 is scraped and inoculated into LB liquid mediums with pH being 7 to be cultivated. After cultivation for 36 h at 20 to 50° C. respectively, $OD_{600}$ values in cultivation solutions are detected through a microplate reader. It is found that a suitable growth temperature of *Microbacterium oleivorans* JWG-G2 is 25 to 40° C., and the most suitable growth temperature is 35° C.

A ring of *Microbacterium oleivorans* JWG-G2 obtained in Example 1 is scraped and inoculated into LB liquid mediums with pH being 7 to be cultivated for 36 h at 35° C. During cultivation, $OD_{600}$ values in cultivation solutions are detected through a microplate reader. It is found that *Microbacterium oleivorans* JWG-G2 has a quick propagation speed, and can enter a stable phase of growth after cultivation for 14 to 16 h.

Example 3: Degradation Abilities of Different Microbacteria and *Microbacterium oleivorans* to Polyethylene Terephthalate (PET) Plastic Particles Specific steps are as follows:

Because *Microbacterium oleivorans* JWG-G2 belongs to a *Microbacterium* and the *Microbacterium* may be one of potential PET plastic particle degradation strain sources, 18 microbacteria with a close affinity to *Microbacterium oleivorans* JWG-G2 are collected and taken as test strains jointly with *Microbacterium oleivorans* JWG-G2.

Single bacterial colonies of *Microbacterium oleivorans* JWG-G2 obtained in Example 1 and the 18 microbacteria are picked, inoculated into 100 mL of LB liquid mediums respectively, and subjected to shaking cultivation for 24 h at 35° C. and 180 rpm to obtain seed solutions A. The seed solutions A are transferred into 100 mL of fresh LB liquid mediums with an inoculation quantity of 10% (v/v), and subjected to shaking cultivation for 24 h at 35° C. and 180 rpm to obtain cultivation solutions A. The cultivation solutions A are centrifuged for 10 min at 8,000 rpm, and thalluses are collected. After the thalluses are washed with an inorganic salt medium for 2 times, bacterial suspensions with $OD_{600}$ being 1.0 are prepared to be taken as seed solutions B. With inorganic salt liquid mediums not inoculated with the seed solutions B and containing 2 g/L PET as control groups, the seed solutions B are inoculated into the inorganic salt liquid mediums containing the 2 g/L PET with an inoculation quantity of 10% (v/v) and subjected to shaking cultivation for 16 d at 35° C. and 180 rpm. During shaking cultivation, sampling is conducted once every 1 d. $OD_{600}$ of cultivation solutions B is determined to obtain growth curves of *Microbacterium oleivorans* JWG-G2 and the 18 microbacteria with the PET plastic particles as a unique nutrient source (see Table 1 for changes of the $OD_{600}$ of *Microbacterium oleivorans* JWG-G2 and the 18 microbacteria before and after cultivation through the inorganic salt liquid mediums containing the 2 g/L PET, and see FIG. 3 for the growth curve of *Microbacterium oleivorans* JWG-G2). At the 5th d, the PET plastic particles in the cultivation solutions B are taken out, changes of structures of functional groups on surfaces of the PET plastic particles are detected (see Table 2 for the changes of the structures of the functional groups on the surfaces of the PET plastic particles in the cultivation solutions B obtained by cultivation of *Microbacterium oleivorans* JWG-G2 and the 18 microbacteria, and see FIG. 4 for the changes of the structures of the functional groups on the surfaces of the PET plastic particles in the cultivation solutions B obtained by cultivation of *Microbacterium oleivorans* JWG-G2), and weight loss ratios of the PET plastic particles are detected (see Table 2 for the weight loss ratios of the PET plastic particles in the cultivation solutions B obtained by cultivation of *Microbacterium oleivorans* JWG-G2 and the 18 microbacteria). At the same time, contents of degradation products MHET and TPA of the PET plastic particles in the cultivation solutions B are detected (see Table 2 for the contents of the degradation products MHET and TPA of the PET plastic particles in the cultivation solutions B obtained by cultivation of *Microbacterium oleivorans* JWG-G2 and the 18 microbacteria).

Figure 3:
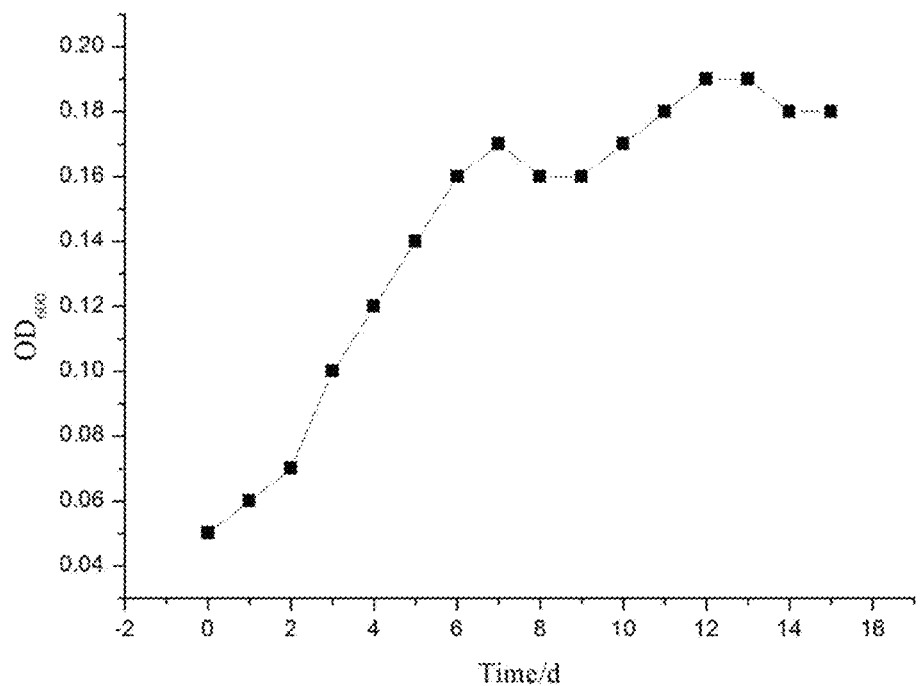
FIG. 3 is a growth curve of the *Microbacterium oleivorans* JWG-G2 with polyethylene terephthalate (PET) plastic particles as a unique nutrient source.

It can be seen from Table 1 and FIG. 3 that with the PET plastic particles as the unique nutrient source, *Microbacterium oleivorans* JWG-G2 enters a logarithmic growth phase at the 2nd to 7th d, then gradually enters a stable phase and slowly increases until balance. $OD_{600}$ of the 18 microbacteria has no significant change (in an error range of ±0.04). It can be seen that only *Microbacterium oleivorans* JWG-G2 can grow and propagate with the PET plastic particles as the unique nutrient source.

Figure 4:
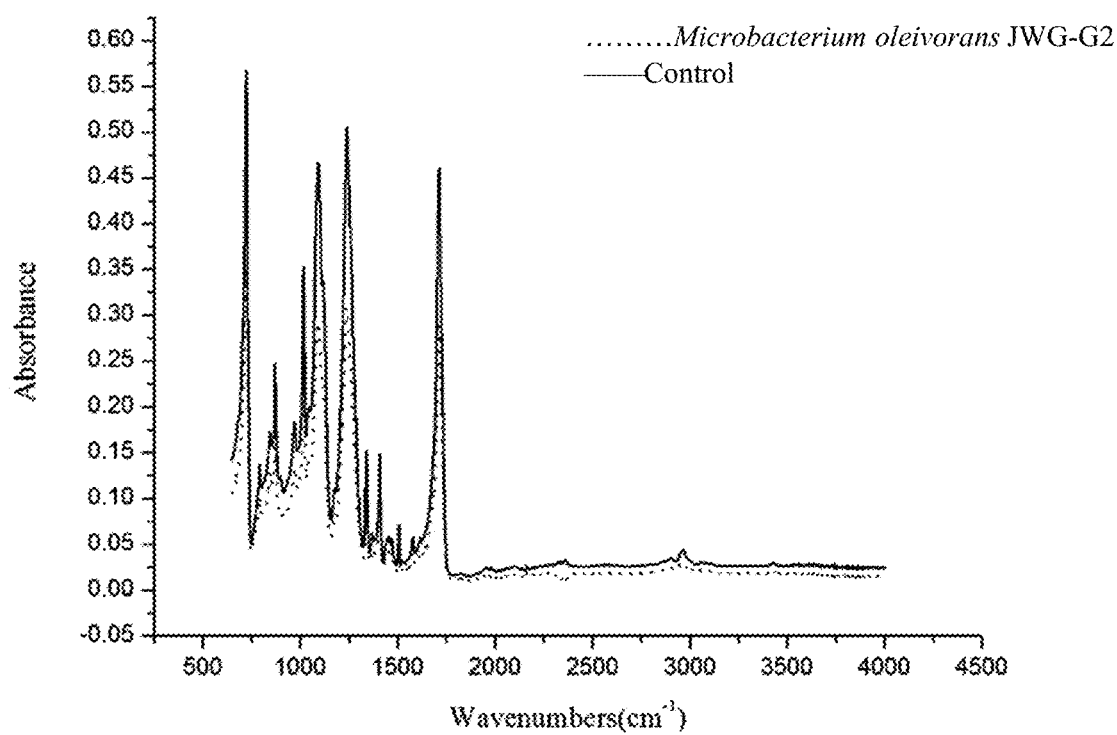
FIG. 4 is a change situation of ester bond functional groups after surfaces of the PET plastic particles are treated by *Microbacterium oleivorans* JWG-G2.

It can be seen from Table 2 and FIG. 4 that after treated for 5 d by *Microbacterium oleivorans* JWG-G2, the PET plastic particles are partially degraded into monohydroxyethyl terephthalate and terephthalic acid capable of being directly recycled, ester bond functional groups on the surfaces of the PET plastic particles are destroyed (there are two characteristic peaks between 1000 to 1300 $cm^{-1}$, and there is one characteristic peak between 1700 to 1750 $cm^{-1}$), and the PET plastic particles lose weight by 5.6%; and after treated for 5 d by the 18 microbacteria, the PET plastic particles have no obvious change. It can be seen that only *Microbacterium oleivorans* JWG-G2 can degrade the PET plastic particles.

TABLE 1

Changes of $OD_{600}$ before and after cultivation of *Microbacterium oleivorans* JWG-G2 and the 18 microbacteria through the inorganic salt liquid mediums containing the 2 g/L PET

| Strains | $OD_{600}$ | Strains | $OD_{600}$ |
| --- | --- | --- | --- |
| *Microbacterium oleivorans* JWG-G2 | 0.2 | *Microbacterium oleivorans* NBRC103075 | 0.02 |
| *Microbacterium hibisci* KACC18931 | 0.02 | *Microbacterium flavescens* DSM20643 | 0.01 |
| *Microbacterium hominis* NBRC15708 | 0.03 | *Microbacterium laevaniformans* DSM20140 | 0.01 |
| *Microbacterium enclense* DSM25125 | 0.03 | *Microbacterium dextranolyticum* DSM8607 | 0.02 |
| *Microbacterium telephonicum* KACC18715 | 0.01 | *Microbacterium saccharophilum* NBRC108778 | 0.01 |
| *Microbacterium ketosireducens* DSM12510 | 0.03 | *Microbacterium terrae* JCM15516 | 0.01 |
| *Microbacterium flavum* JCM15574 | 0.03 | *Microbacterium diaminobutyricum* DSM27101 | 0.01 |
| *Microbacterium schleiferi* DSM20489 | 0.01 | *Microbacterium lacticum* DSM20427 | 0.01 |
| *Microbacterium terregens* JCM1342 | 0.01 | *Microbacterium aurum* KACC15219 | 0.01 |
| *Microbacterium aoyamense* JCM14900 | 0.01 | | |

The changes of the $OD_{600}$ before and after cultivation of *Microbacterium oleivorans* JWG-G2 and the 18 microbacteria through the inorganic salt liquid mediums containing the 2 g/L PET are obtained by subtracting $OD_{600}$ values before cultivation of *Microbacterium oleivorans* JWG-G2 and the 18 microbacteria through the inorganic salt liquid mediums containing the 2 g/L PET from $OD_{600}$ values after cultivation of *Microbacterium oleivorans* JWG-G2 and the 18 microbacteria through the inorganic salt liquid mediums containing the 2 g/L PET.

TABLE 2

Contents of the degradation products MHET and TPA of the PET plastic particles in the cultivation solutions B obtained by cultivation of *Microbacterium oleivorans* JWG-G2 and the 18 microbacteria, changes of the structures of the functional groups on the surfaces of the PET plastic particles, and weight loss ratios of the PET plastic particles

| Categories | Contents of degradation products (mg/L) | | PET weight loss ratios (%) | Ester bond functional groups |
|---|---|---|---|---|
| | TPA | MHET | | |
| *Microbacterium oleivorans* JWG-G2 | 1.3 | 6.9 | 1 | + |
| *Microbacterium oleivorans* NBRC103075 | – | – | – | – |
| *Microbacterium hibisci* KACC18931 | – | – | – | – |
| *Microbacterium flavescens* DSM20643 | – | – | – | – |
| *Microbacterium hominis* NBRC15708 | – | – | – | – |
| *Microbacterium laevaniformans* DSM20140 | – | – | – | – |
| *Microbacterium enclense* DSM25125 | – | – | – | – |
| *Microbacterium dextranolyticum* DSM8607 | – | – | – | – |
| *Microbacterium telephonicum* KACC18715 | – | – | – | – |
| *Microbacterium saccharophilum* NBRC108778 | – | – | – | – |
| *Microbacterium ketosireducens* DSM12510 | – | – | – | – |
| *Microbacterium terrae* JCM15516 | – | – | – | – |
| *Microbacterium flavum* JCM15574 | – | – | – | – |
| *Microbacterium diaminobutyricum* DSM27101 | – | – | – | – |
| *Microbacterium schleiferi* DSM20489 | – | – | – | – |
| *Microbacterium lacticum* DSM20427 | – | – | – | – |
| *Microbacterium terregens* JCM1342 | – | – | – | – |
| *Microbacterium aurum* KACC15219 | – | – | – | – |
| *Microbacterium aoyamense* JCM14900 | – | – | – | – |

"+": detection is positive; and
"–": detection is negative.

Example 4: Degradation Abilities of *Microbacterium oleivorans* JWG-G2 to Polyethylene Terephthalate (PET) Plastic Particle Intermediate Specific steps are as follows:

Single bacterial colonies of *Microbacterium oleivorans* JWG-G2 obtained in Example 1 and 18 microbacteria are picked, inoculated into 100 mL of LB liquid mediums respectively, and subjected to shaking cultivation for 24 h at 35° C. and 180 rpm to obtain seed solutions A. The seed solutions A are transferred into 100 mL of fresh LB liquid mediums with an inoculation quantity of 10% (v/v), and subjected to shaking cultivation for 24 h at 35° C. and 180 rpm to obtain cultivation solutions A. The cultivation solutions A are centrifuged for 10 min at 8000 rpm, and thalluses are collected. After the thalluses are washed with an inorganic salt medium for 2 times, bacterial suspensions with $OD_{600}$ being 1.0 are prepared to be taken as seed solutions B. The seed solutions B are inoculated into inorganic salt liquid mediums containing 0.2 g/L MHET or 0.2 g/L BHET (the MHET and the BHET are both PET intermediates) respectively with an inoculation quantity of 10% (v/v) and subjected to shaking cultivation for 5 d at 35° C. and 180 rpm to obtain cultivation solutions B.

The MHET and the BHET in the cultivation solutions B are taken out, and their weight loss ratios are detected. At the same time, changes of components in the cultivation solutions B are analyzed by HPLC (see FIGS. 5 to 6 for analysis results).

It can be known from the analysis results of the weight loss ratios that after 5 d of treatment through *Microbacterium oleivorans* JWG-G2, the weight loss ratio of the MHET reaches 4.5%, and the weight loss ratio of the BHET reaches 11.2%. It can be seen that e *Microbacterium oleivorans* JWG-G2 can degrade the MHET and the BHET.

Figure 5:
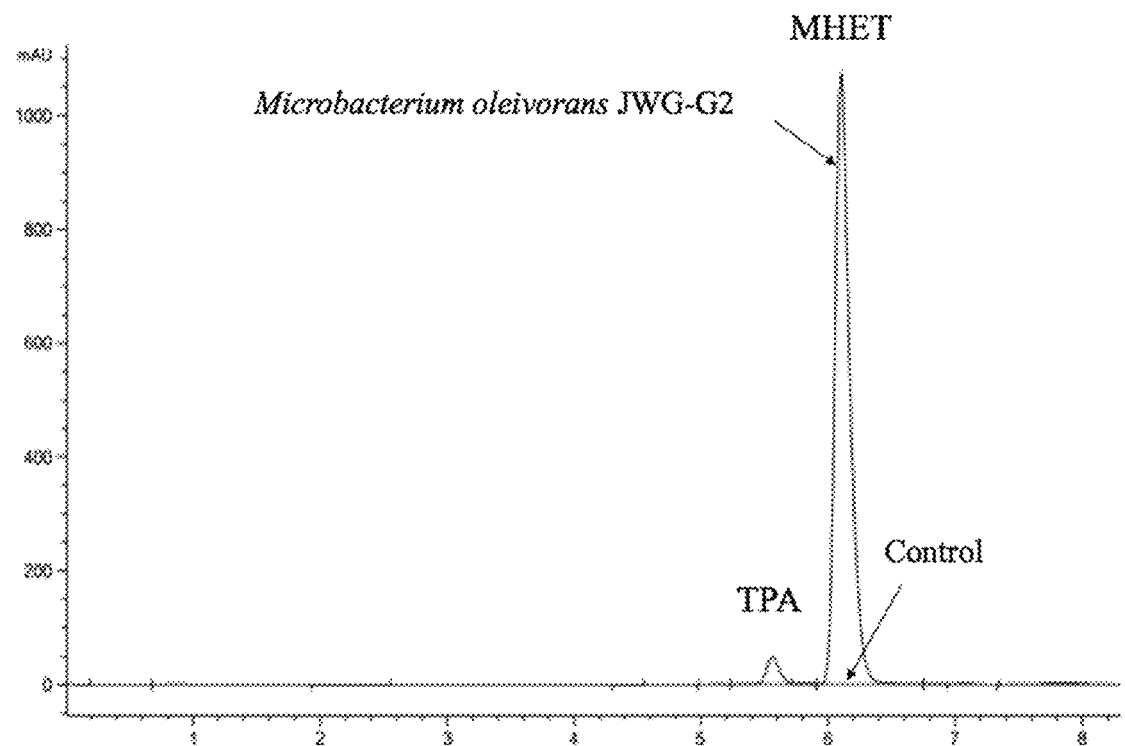
FIG. 5 is a degradation product after monohydroxyethyl terephthalate (MHET) is treated by *Microbacterium oleivorans* JWG-G2.

It can be known from FIG. 5 that after treated by *Microbacterium oleivorans* JWG-G2 for 5 d, the MHET is partially degraded into terephthalic acid (TPA) capable of being directly recycled, and the content of the TPA in the cultivation solutions B is 8.25 mg/L, which further proves that *Microbacterium oleivorans* JWG-G2 can degrade the MHET.

Figure 6:
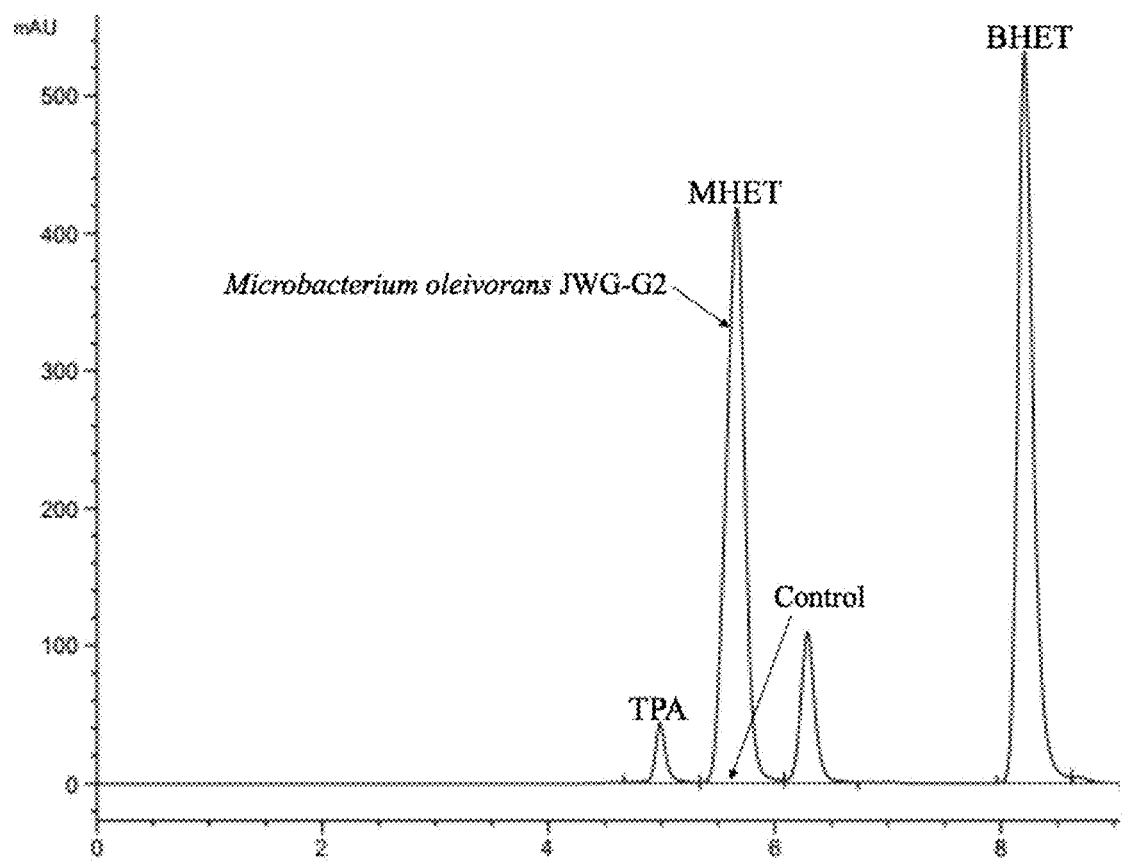
FIG. 6 is degradation products after bis(2-hydroxyethyl) terephthalate (BHET) is treated by *Microbacterium oleivorans* JWG-G2.

It can be known from FIG. 6 that after treated by *Microbacterium oleivorans* JWG-G2 for 5 d, the BHET is partially degraded into MHET and TPA capable of being directly recycled, and the contents of the MHET and the TPA in the cultivation solutions B are 16.56 mg/L and 3.81 mg/L respectively, which further proves that *Microbacterium oleivorans* JWG-G2 can degrade the BHET.

Example 5: Salt Resistance of *Microbacterium oleivorans* JWG-G2

Specific steps are as follows:

Single bacterial colonies of *Microbacterium oleivorans* JWG-G2 obtained in Example 1 are picked, inoculated into 100 mL of LB liquid mediums, and subjected to shaking cultivation for 24 h at 35° C. and 180 rpm to obtain seed solutions A. The seed solutions A are transferred into 100 mL of fresh LB liquid mediums with an inoculation quantity of 10% (v/v), and subjected to shaking cultivation for 72 h at 35° C. and 180 rpm to obtain cultivation solutions A. The cultivation solutions A are centrifuged for 10 min at 8,000 rpm, and thalluses are collected. After the thalluses are washed with an inorganic salt medium for 2 times, bacterial suspensions with $OD_{600}$ being 1.0 are prepared to be taken as seed solutions B. The seed solutions B are inoculated into LB liquid mediums containing different concentrations of NaCl (1, 2, 3, 4, 5, 6, 7, 8, 9, and 10 g/L) respectively with an inoculation quantity of 10% (v/v) and subjected to shaking cultivation for 5 d at 35° C. and 180 rpm to obtain cultivation solutions B.

It is found from results of determining $OD_{600}$ of the cultivation solutions B that $OD_{600}$ increments in the cultivation solutions B obtained after *Microbacterium oleivorans* JWG-G2 grows for 5 d in the LB liquid mediums containing 1 to 9 g/L NaCl are 0.11, 0.12, 0.18, 0.2, 0.23, 0.18, 0.15, 0.1 and 0.1 respectively. It can be seen that *Microbacterium oleivorans* JWG-G2 has excellent salt resistance.

Example 6: Abilities of *Microbacterium oleivorans* JWG-G2 to Degrade Starch and Liquidize Gelatin Specific steps are as follows:

The abilities of *Microbacterium oleivorans* JWG-G2 to degrade the starch and liquidize the gelatin are detected through a plate transparent zone method according to a reference "Journal of Microbiology, 2014, 34(01): 28-32; Tang Yu, Southwest University, 2007".

It can be known from detection results that after *Microbacterium oleivorans* grows for 5 d on detection plates, there are obvious hydrolyzed transparent zones on surfaces of the plates, and diameters of starch and gelatin transparent zones reach 1.1 cm and 1.6 cm respectively. It can be seen that *Microbacterium oleivorans* JWG-G2 has the abilities to degrade the starch and liquidize the gelatin.

---

What is claimed is:

1. A method for degrading polyethylene terephthalate and/or an intermediate of the polyethylene terephthalate, which comprises:
   inoculating *Microbacterium oleivorans* into a medium for cultivation,
   wherein the medium comprises polyethylene terephthalate (PET), an intermediate of the PET, or both;
   wherein the intermediate of the PET is monohydroxyethyl terephthalate (MHET), bis(2-hydroxyethyl) terephthalate (BHET), or both; and
   wherein the *Microbacterium oleivorans* is *Microbacterium oleivorans* deposited with the China Center for Type Culture Collection (CCTCC), with CCTCC deposit number M 2019416.

2. The method according to claim 1, wherein the medium is a liquid medium.

3. The method according to claim 1, wherein an inoculation quantity of *Microbacterium oleivorans* in the medium is not less than $1\times10^8$ CFU/mL.

4. The method according to claim 1, wherein the medium comprises the PET, and a content of the PET is not greater than 2 g/L.

5. The method according to claim 1, wherein the medium comprises the intermediate of the PET, and a content of the intermediate of the PET is not greater than 0.2 g/L.

6. The method according to claim 1, wherein the medium comprises the PET and the intermediate of the PET, and a total content of the PET and the intermediate of the PET is not greater than 2.2 g/L.

7. The method according to claim 1, wherein the medium is an inorganic salt medium.

* * * * *

SEQUENCE LISTING

```
<160> NUMBER OF SEQ ID NOS: 1

<210> SEQ ID NO 1
<211> LENGTH: 1384
<212> TYPE: DNA
<213> ORGANISM: Microbacterium oleivorans

<400> SEQUENCE: 1
agtcgaacgg tgaagcccag cttgctgggt ggatcagtgg cgaacgggtg agtaacacgt    60
gagcaatctg cccctgactc tgggataagc gctggaaacg gtgtctaata ctggatatga   120
gctgcgaccg catggtcagt agttggaaag atttttcggt cagggatgag ctcgcggcct   180
atcagcttgt tggtgaggta atggctcacc aaggcgtcga cgggtagccg gcctgagagg   240
gtgaccggcc acactgggac tgagacacgg cccagactcc tacgggaggc agcagtgggg   300
aatattgcac aatgggcgga agcctgatgc agcaacgccg cgtgagggat gacggccttc   360
gggttgtaaa cctcttttag cagggaagaa gcgaaagtga cggtacctgc agaaaaagcg   420
ccggctaact acgtgccagc agccgcggta atacgtaggg cgcaagcgtt atccggaatt   480
attgggcgta aagagctcgt aggcggtttg tcgcgtctgc tgtgaaatcc cgaggctcaa   540
cctcgggcct gcagtgggta cgggcagact agagtgcggt aggggagatt ggaattcctg   600
gtgtagcggt ggaatgcgca gatatcagga ggaacaccga tggcgaaggc agatctctgg   660
gccgtaactg acgctgagga gcgaaagggt ggggagcaaa caggcttaga taccctggta   720
gtccaccccg taaacgttgg gaactagttg tggggtccat tccacggatt ccgtgacgca   780
gctaacgcat taagttcccc gcctggggag tacggccgca aggctaaaac tcaaaggaat   840 tgacgggac ccgcacaagc ggcggagcat gcggattaat tcgatgcaac gcgaagaacc   900
ttaccaaggc ttgacatata cgagaacggg ccagaaatgg tcaactcttt ggacactcgt   960
aaacaggtgg tgcatggttg tcgtcagctc gtgtcgtgag atgttgggtt aagtcccgca  1020
acgagcgcaa ccctcgttct atgttgccag cacgtaatgg tgggaactca tgggatactg  1080
ccggggtcaa ctcggaggaa ggtggggatg acgtcaaatc atcatgcccc ttatgtcttg  1140
ggcttcacgc atgctacaat ggccggtaca aagggctgca ataccgtgag gtggagcgaa  1200
tcccaaaaag ccggtcccag ttcggattga ggtctgcaac tcgacctcat gaagtcggag  1260
```

```
                                                              -continued
tcgctagtaa tcgcagatca gcaacgctgc ggtgaatacg ttcccgggtc ttgtacacac    1320
cgcccgtcaa gtcatgaaag tcggtaacac ctgaagccgg tggcctaacc cttgtggagg    1380
gagc                                                                 1384
```